(12) United States Patent
Jansen et al.

(10) Patent No.: US 6,319,233 B1
(45) Date of Patent: Nov. 20, 2001

(54) SAFETY SHIELD SYSTEM FOR PREFILLED SYRINGES

(75) Inventors: Hubert Jansen, Poisat; Samuel Gagnieux, Le Pont de Claix, both of (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/290,786

(22) Filed: Apr. 12, 1999

Related U.S. Application Data

(60) Provisional application No. 60/082,221, filed on Apr. 17, 1998.

(51) Int. Cl.[7] .................................................... A61M 5/32
(52) U.S. Cl. ............................................ 604/192; 604/187
(58) Field of Search .............................. 604/40, 43, 192, 604/193, 194, 198, 110, 263, 187, 195

(56) References Cited

U.S. PATENT DOCUMENTS

| | | |
|---|---|---|
| Re. 34,045 | 8/1992 | McFarland . |
| 2,801,741 | 8/1957 | Harkness et al. . |
| 4,285,105 | 8/1981 | Kirkpatrick . |
| 4,425,120 | 1/1984 | Sampson et al. . |
| 4,573,976 | 3/1986 | Sampson et al. . |
| 4,585,445 | 4/1986 | Hadtke . |
| 4,631,057 | 12/1986 | Mitchell . |
| 4,723,943 | 2/1988 | Spencer . |
| 4,737,144 | 4/1988 | Choksi . |
| 4,743,233 | 5/1988 | Scheider . |
| 4,747,837 | 5/1988 | Hauck . |
| 4,758,231 | 7/1988 | Haber et al. . |
| 4,801,295 | 1/1989 | Spencer . |
| 4,826,491 | 5/1989 | Schramm . |
| 4,840,185 | 6/1989 | Hernandez . |
| 4,850,994 | 7/1989 | Zerbst et al. . |
| 4,863,434 | 9/1989 | Bayless . |
| 4,871,355 | 10/1989 | Kikkawa . |
| 4,900,310 | 2/1990 | Ogle, II . |
| 4,917,673 | 4/1990 | Coplin . |
| 4,923,445 | 5/1990 | Ryan . |
| 4,923,447 | 5/1990 | Morgan . |
| 4,927,018 | 5/1990 | Yang et al. . |
| 4,932,937 | 6/1990 | Gustavsson et al. . |
| 4,947,863 | 8/1990 | Haber et al. . |

(List continued on next page.)

FOREIGN PATENT DOCUMENTS

| | | |
|---|---|---|
| 52050/96 | 11/1996 | (AU) . |
| 0 467 173 A1 | 1/1994 | (EP) . |
| 0 645 155 A2 | 3/1995 | (EP) . |
| 0 740 942 A1 | 11/1996 | (EP) . |
| 0 740 942 B1 | 11/1996 | (EP) . |
| 0 864 335 A2 | 9/1998 | (EP) . |
| WO 92/19296 | 11/1992 | (WO) . |
| WO 97/14455 | 4/1997 | (WO) . |
| WO 98/35714 | 8/1998 | (WO) . |
| WO 99/16489 | 4/1999 | (WO) . |
| WO 00/33900 | 6/2000 | (WO) . |

*Primary Examiner*—Richard K. Seidel
*Assistant Examiner*—Kevin Sirmons
(74) *Attorney, Agent, or Firm*—Allen W. Wark

(57) ABSTRACT

A medical device is provided which includes a shield system and a syringe which is coupled to the shield system. The shield system includes a syringe holder and a shield which is slidably coupled to the holder. A spring resiliently urges the shield from a retracted position to an extended position. Stop members are provided on the holder and shield for maintaining the shield in the retracted position. The syringe is slidably coupled to the holder, and extends within the shield. Axial movement of the syringe with respect to the holder causes disengagement of the stop members, allowing the spring to move the shield to the extended position. Detents are provided on the holder for maintaining the shield in the extended position.

21 Claims, 19 Drawing Sheets

U.S. PATENT DOCUMENTS

| | | |
|---|---|---|
| 4,985,021 | 1/1991 | Straw et al. . |
| 4,994,045 | 2/1991 | Ranford . |
| 4,998,920 | 3/1991 | Johnson . |
| 4,998,924 | 3/1991 | Ranford . |
| 5,019,051 | 5/1991 | Hake . |
| 5,024,660 | 6/1991 | McNaughton . |
| 5,045,066 | 9/1991 | Scheuble et al. . |
| 5,053,018 | 10/1991 | Talonn et al. . |
| 5,057,086 | 10/1991 | Dillard, III et al. . |
| 5,057,087 | 10/1991 | Harmon . |
| 5,059,185 | 10/1991 | Ryan . |
| 5,066,277 | 11/1991 | Carrell et al. . |
| 5,067,945 | 11/1991 | Ryan et al. . |
| 5,078,698 | 1/1992 | Stiehl et al. . |
| 5,084,030 | 1/1992 | Byrne et al. . |
| 5,106,379 | 4/1992 | Leap . |
| 5,108,378 | 4/1992 | Firth et al. . |
| 5,137,521 | 8/1992 | Wilkins . |
| 5,141,500 | 8/1992 | Hake . |
| 5,147,303 | 9/1992 | Martin . |
| 5,163,918 | 11/1992 | Righi et al. . |
| 5,169,392 | 12/1992 | Ranford et al. . |
| 5,188,614 | 2/1993 | Hart . |
| 5,197,953 | 3/1993 | Colonna . |
| 5,201,708 | 4/1993 | Martin . |
| 5,201,720 | 4/1993 | Borgia et al. . |
| 5,217,437 | 6/1993 | Talonnn et al. . |
| 5,226,894 | 7/1993 | Haber et al. . |
| 5,242,420 | 9/1993 | Martin . |
| 5,256,154 | 10/1993 | Liebert et al. . |
| 5,279,581 | 1/1994 | Firth et al. . |
| 5,300,030 * | 4/1994 | Crossman et al. .................. 604/136 |
| 5,300,040 | 4/1994 | Morigi . |
| 5,304,147 | 4/1994 | Morigi . |
| 5,308,332 | 5/1994 | Dillard, III et al. . |
| 5,312,365 | 5/1994 | Firth et al. . |
| 5,318,538 | 6/1994 | Martin . |
| 5,318,547 | 6/1994 | Altschuler . |
| 5,338,303 | 8/1994 | King et al. . |
| 5,338,310 | 8/1994 | Lewandowski . |
| 5,342,309 | 8/1994 | Hausser . |
| 5,342,320 | 8/1994 | Cameron . |
| 5,344,407 | 9/1994 | Ryan . |
| 5,346,480 | 9/1994 | Hess et al. . |
| 5,348,544 | 9/1994 | Sweeney et al. . |
| 5,350,367 | 9/1994 | Stiehl et al. . |
| 5,352,208 | 10/1994 | Robinson . |
| 5,356,392 | 10/1994 | Firth et al. . |
| 5,358,491 | 10/1994 | Johnson et al. . |
| 5,368,578 | 11/1994 | Covington et al. . |
| 5,380,296 | 1/1995 | Smedley et al. . |
| 5,385,555 | 1/1995 | Hausser . |
| 5,385,557 | 1/1995 | Thompson . |
| 5,411,488 | 5/1995 | Pagay et al. . |
| 5,411,489 | 5/1995 | Pagay et al. . |
| 5,413,563 | 5/1995 | Basile et al. . |
| 5,417,660 | 5/1995 | Martin . |
| 5,437,647 | 8/1995 | Firth et al. . |
| 5,439,450 | 8/1995 | Haedt . |
| 5,447,500 | 9/1995 | Bergstresser et al. . |
| 5,458,577 | 10/1995 | Kishigami . |
| 5,478,316 * | 12/1995 | Bitdinger et al. .................. 604/135 |
| 5,496,286 | 3/1996 | Stiehl et al. . |
| 5,501,672 | 3/1996 | Firth et al. . |
| 5,527,294 | 6/1996 | Weatherford et al. . |
| 5,562,624 | 10/1996 | Righi et al. . |
| 5,562,626 | 10/1996 | Sampietro . |
| 5,601,535 | 2/1997 | Byrne et al. . |
| 5,611,782 | 3/1997 | Haedt . |
| 5,616,134 | 4/1997 | Firth et al. . |
| 5,624,400 | 4/1997 | Firth et al. . |
| 5,647,849 | 7/1997 | Kalin . |
| 5,658,254 | 8/1997 | Reicjenbach et al. . |
| 5,674,203 | 10/1997 | Lewandowski . |
| 5,681,292 | 10/1997 | Tober et al. . |
| 5,697,908 | 12/1997 | Imbert et al. . |
| 5,709,662 * | 1/1998 | Olive et al. .................. 604/135 |
| 5,713,871 | 2/1998 | Stock . |
| 5,733,264 | 3/1998 | Flowers . |
| 5,735,823 | 4/1998 | Bergen . |
| 5,769,822 | 6/1998 | McGary et al. . |
| 5,769,827 | 6/1998 | DeMichele et al. . |
| 5,776,107 | 7/1998 | Cherif-Cheikh . |
| 5,788,677 | 8/1998 | Botich et al. . |
| 5,792,107 | 8/1998 | Petrocelli . |
| 5,792,122 | 8/1998 | Brimhall et al. . |
| 5,795,336 * | 8/1998 | Romano et al. .................. 604/192 |
| 5,797,885 | 8/1998 | Rubin . |
| 5,800,395 | 9/1998 | Botich et al. . |
| 5,800,403 | 9/1998 | Pressly, Sr. et al. . |
| 5,800,404 | 9/1998 | Poulsen . |
| 5,810,775 | 9/1998 | Shaw . |
| 5,817,064 | 10/1998 | DeMarco et al. . |
| 5,843,034 | 12/1998 | Redfern et al. . |
| 5,843,036 * | 12/1998 | Olive et al. .................. 604/136 |
| 5,843,041 | 12/1998 | Hake et al. . |
| 5,843,047 | 12/1998 | Pyrozyk et al. . |
| 5,853,390 | 12/1998 | Freschi . |
| 5,855,839 | 1/1999 | Brunel . |
| 5,868,713 | 2/1999 | Klippenstein . |
| 5,879,339 | 3/1999 | Saito . |
| 5,882,342 | 3/1999 | Cooper et al. . |
| 5,910,130 * | 6/1999 | Caizza et al. .................. 604/110 |
| 5,947,936 | 9/1999 | Bonds . |
| 5,980,494 | 11/1999 | Malenchek et al. . |
| 5,984,898 | 11/1999 | Garvin . |
| 5,984,899 * | 11/1999 | D'Alessio et al. .................. 604/198 |
| 5,984,906 | 11/1999 | Bonnichsen et al. . |
| 6,004,296 | 12/1999 | Jansen et al. . |
| 6,010,487 | 1/2000 | DeMichele et al. . |
| 6,017,329 * | 1/2000 | Hake .................. 604/198 |
| 6,030,366 | 2/2000 | Mitchell . |
| 6,033,387 | 3/2000 | Brunel . |

* cited by examiner

SAFETY SHIELD SYSTEM FOR PREFILLED SYRINGES

This application claims benefit of Provisional No. 60/082,221 filed Apr. 17, 1998.

BACKGROUND OF THE INVENTION

1. Field of the Invention

The field of the invention relates to shield systems for protecting against needle sticks, and syringes including such systems.

2. Brief Description of the Related Art

Syringes are well known medical devices for administering medicaments to patients. They are also used for other well known purposes in the field of medicine. Prefilled syringes are generally considered as those which are filled with a selected dosage of medicament or other substance by a pharmaceutical manufacturer for distribution to the end user. They are often comprised of a glass or plastic barrel which contains the medicament or other substance and a piston slidably mounted within the barrel. One end of the barrel includes a needle or the like affixed thereto or a connector for a needle assembly such as a Luer fitting. The term "needle" as used herein should accordingly be construed broadly to include various types of piercing elements or connectors, whether sharp pointed or blunt. The other end of the syringe is open to allow the insertion of a plunger rod. The plunger rod allows the user to apply manual force to the piston, causing the medicament to be delivered through the needle or other piercing element.

The use of a sharp-pointed piercing element entails the risk of accidental needle stick. To avoid such accidents, many prior art hypodermic syringes have included rigid cylindrical safety shields telescoped over the syringe barrel. These shields can be moved between retracted positions where the needles are exposed for use, to extended positions where the needles are surrounded by the shields. U.S. Pat. Nos. 4,425,120, 4,573,976, 4,850,994 and 4,923,447 disclose various shield systems for hypodermic syringes. The latter two patents disclose shields which are spring-actuated. It is ordinarily desirable to lock the needle shields in the protected positions, and a number of prior art designs provide for such locking. Some systems, such as those disclosed in U.S. Pat. Nos. 5,201,708, 5,242,240 and 5,318,538 are designed to allow the shields to be retracted from their locked, extended positions.

A shield system for protecting the piercing element of a prefilled syringe is disclosed in European Publication No. EP 0 740 942 A1. The disclosed system includes a holder which is coupled to the flange of the syringe barrel, and a shield which is telescopically mounted to the holder. Two hands are required to operate this system

SUMMARY OF THE INVENTION

The invention relates to a safety shield system for a syringe, and such a system as used in combination with an assembly capable of functioning as a syringe. In accordance with the preferred embodiments of the system, the user is able to cause the shielding of a needle by simply applying pressure to the plunger rod of the syringe following injection of the contents of the syringe barrel. The shield may accordingly be deployed automatically through the use of only one hand. As there is no need to place the hand near the needle for any purpose, the risk of needle stick injury is reduced.

In accordance with the objects of the invention, a medical device is provided which includes an automatically operable shield system mounted to a syringe barrel. The system includes a holder which defines an enclosure. The syringe barrel extends at least partially, and preferably almost entirely, within the enclosure. The barrel is slidable within the holder. A retaining member is positioned on the holder, and is engageable with the barrel. This member prevents the barrel from being uncoupled from the holder. A shield is mounted to the holder, and positioned about at least a portion of the barrel. The shield is axially movable with respect to the holder between retracted and extended positions. It is intended to cover the needle tip when in the extended position. A spring engages the shield, and urges it towards the extended position. A first stop member is positioned on the shield, and a second stop member is positioned on the holder. The second stop member is engageable with the first stop member when the shield is in the retracted position. The force of the spring, by itself, is insufficient to cause disengagement of the first and second stop members. The barrel is operationally coupled to the shield such that sufficient axial movement of the barrel causes axial movement of the shield sufficient to cause disengagement of the first and second stop members. Such movement of the barrel is ordinarily caused by pressure exerted on the plunger rod by the user of the syringe following complete injection of the contents of the barrel. Upon disengagement of the first and second stop members, the spring causes the shield to move to the extended position.

The proximal end of the holder is preferably adapted to engage and retain the flange which may be present at the proximal end of the syringe barrel. The axial movement of the shield is preferably limited by a set of locking detents formed on the holder. Such movement could alternatively be limited by a tether connecting the holder and shield. The shield is preferably positioned within the holder such that the spring engages the first stop member. The opposite end of the spring can bear against any suitable surface, such as the flange on the syringe barrel, if present, or a collar portion of an end fitting slidably positioned within the holder.

The shield system according to the invention is comprised of a holder, a shield, a spring and, preferably, an end fitting. The holder is adapted for receiving at least a flanged portion of the barrel of a syringe, and includes axially spaced, opposing abutment surfaces to retain the flange. The distance between these surfaces corresponds to the distance the syringe can be axially moved with respect to the holder once mounted thereto. The shield is slidably mounted to the holder, and is movable between retracted and extended positions. A spring urges the shield towards the extended position. The holder includes a stop member which is engageable with the shield to maintain it in the retracted position. Sufficient axial movement of the shield causes disengagement of the stop member, allowing the spring to move the shield to the extended position. An end fitting is preferably incorporated in the system to maintain the position of the spring prior to insertion of a syringe into the holder.

The shield system facilitates the safe use of prefilled syringes, though it can be adapted for other sharp-pointed medical devices, such as syringes filled just before use, as well. When employed with a syringe, the system allows the contents of the syringe to be expressed in a conventional manner. Continued, and preferably increased pressure exerted by the user on the plunger rod following injection causes the syringe barrel to move axially, thereby axially displacing the shield. Such displacement causes release of the stop member, and the spring to move the shield over the needle of the syringe. Protection against needle sticks is accordingly provided.

DETAILED DESCRIPTION OF THE INVENTION

Figure 1:
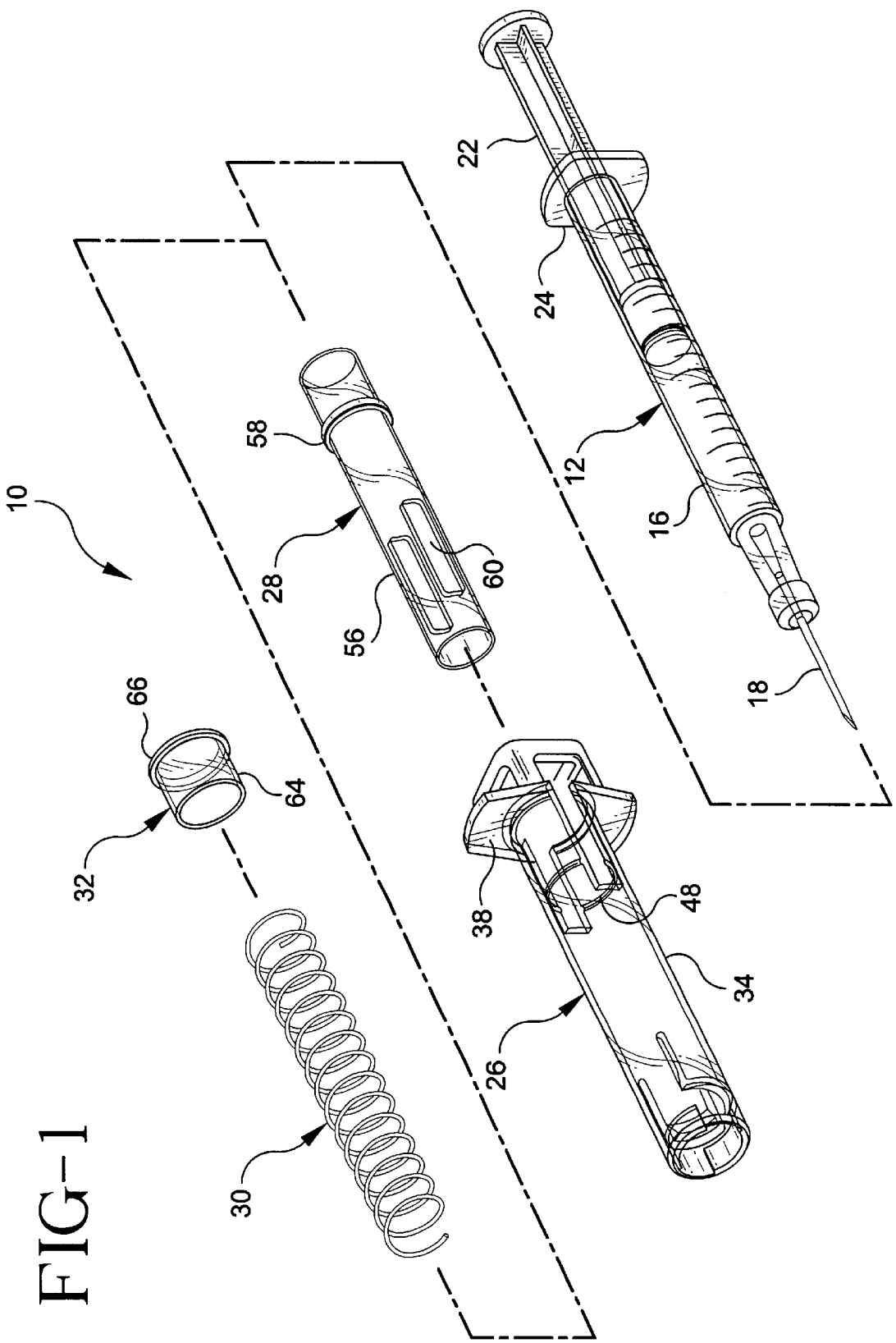
FIG. 1 is an exploded, perspective view showing a medical device according to a first embodiment of the invention.
Figure 2:
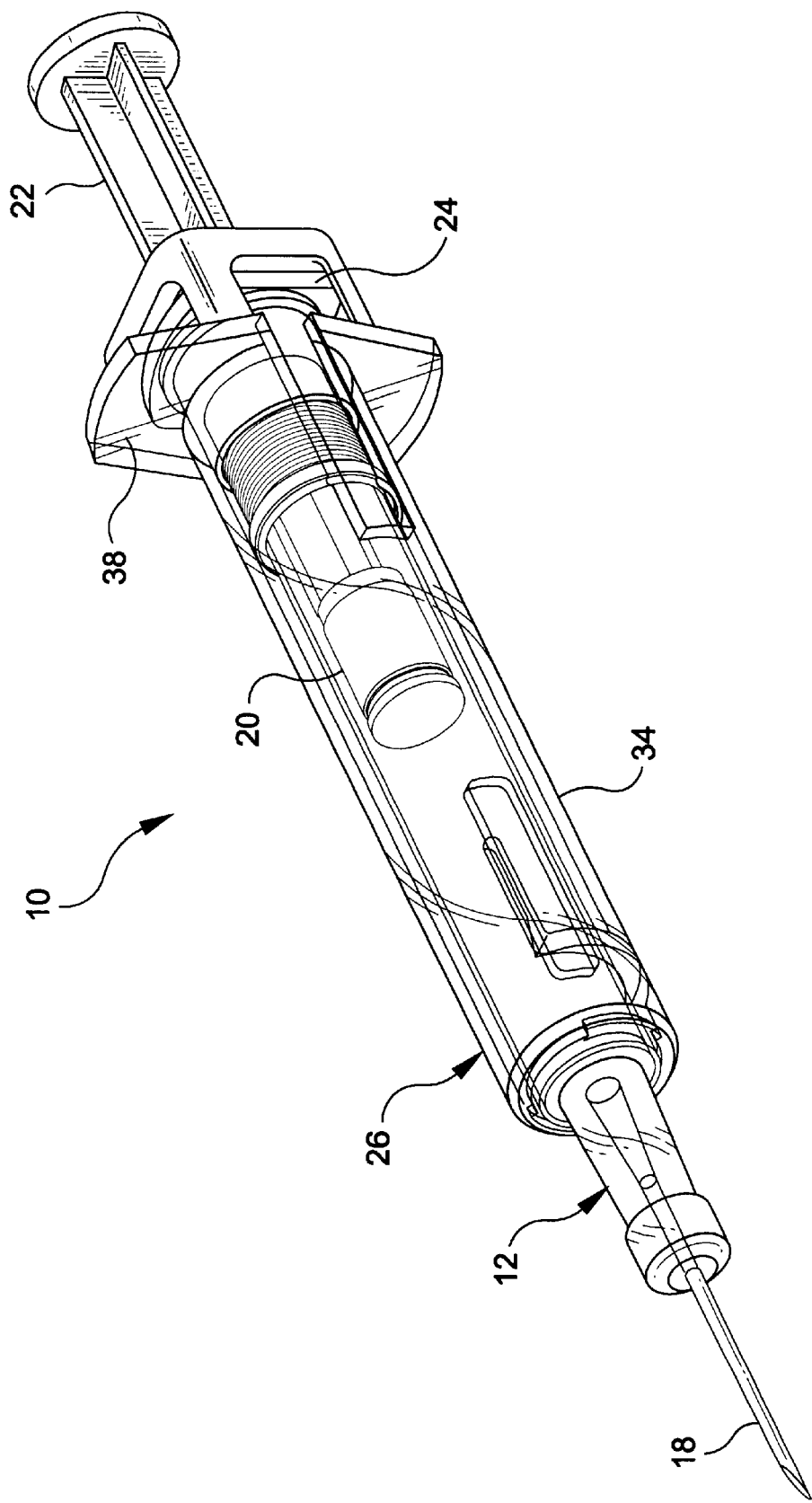
FIG. 2 is a top perspective view of the medical device as assembled.
Figure 3:
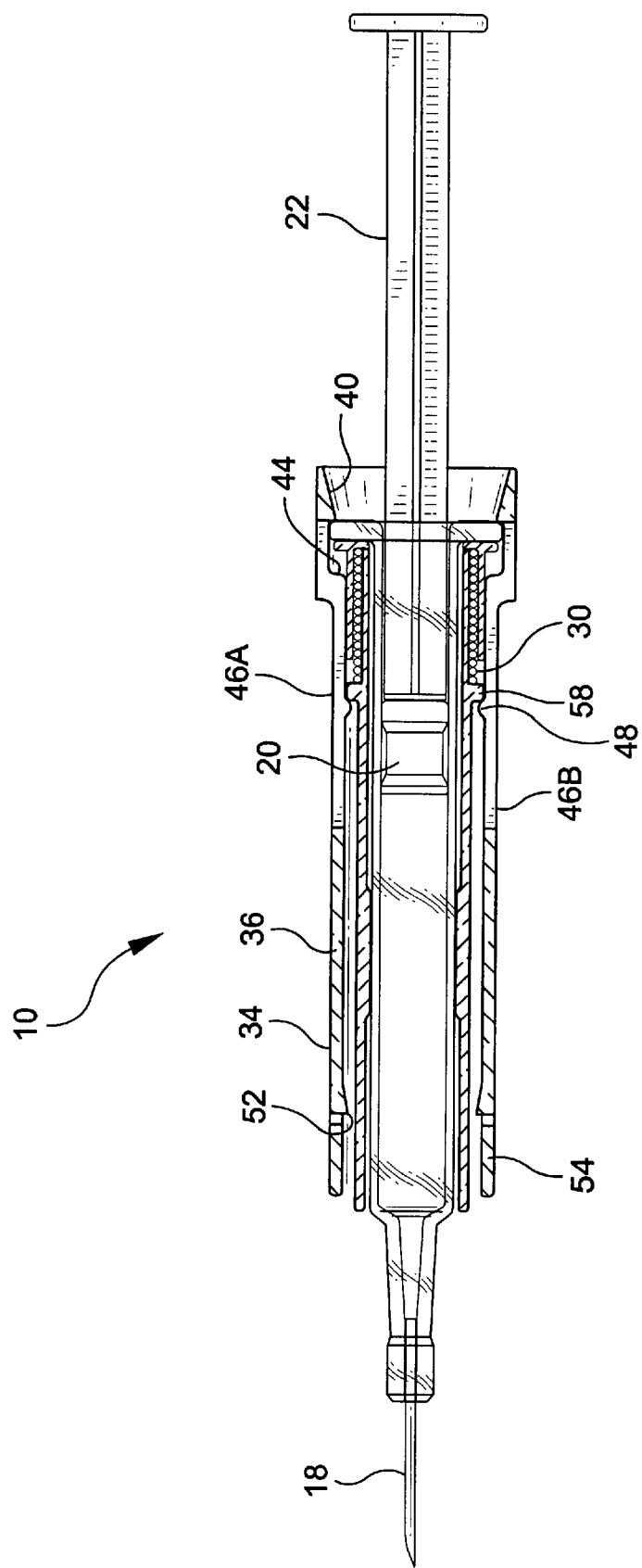
FIG. 3 is a sectional elevation view thereof.

A medical device 10 for injecting a medicament into a patient is shown in FIGS. 1–11. The device comprises a prefillable syringe 12 and a shield system 14 coupled to the syringe.

Syringes are ordinarily comprised of a generally cylindrical portion, known as a barrel, a needle or other piercing or connecting element secured to one end of the barrel, and a piston or stopper slidably positioned within the barrel. The needle may be removably secured to the barrel, but is more likely to be permanently secured to the barrel when the barrel is comprised of glass. Glass barrels are commonly used in prefillable syringes, and ordinarily contain a single dose of medication. Prefilled syringes made from plastic are also known to the art. The shield system 14 disclosed herein is employed in conjunction with a prefilled syringe including a barrel 16, a cannula such as a needle 18 permanently secured to the barrel, a piston 20 slidably positioned within the barrel, and a plunger rod 22 engageable with the piston. The syringe barrel 16 includes a radially outwardly extending flange 24, which is used to couple the syringe to the shield system.

The shield system 14 according to the invention includes a holder 26, a shield 28 coupled to the holder, and a spring 30. It also preferably includes a holder end fitting 32 which engages one end of the spring. With the exception of the spring, all of the components of the system are made from a semi-rigid plastic material such as polypropylene. The spring is preferably a metal coil spring.

The holder 26 is preferably comprised of an elongate, generally cylindrical body 34 which defines a generally cylindrical enclosure 36. The holder has first and second open ends which provide access to the enclosure. A flange 38 extends radially outwardly from the holder body near the second open end thereof. The flange and body of the holder are designed for easy handling as an injection is made. Only one hand should be required for injection.

The inner surface of the holder includes a frustoconical portion 40 adjoining the second open end. A first abutment surface 42 is formed at the inner end of this surface. A second abutment surface 44 is formed by the holder body in opposing relation to the first abutment surface. As described below, the axial spacing between these surfaces corresponds, though is not equal to the axial distance which the syringe can move with respect to the holder. The inner diameter of the holder, measured at the abutment surfaces, is smaller than the distance between the edges of the syringe flange 24. Accordingly, once the syringe is inserted far enough into the holder that the flange 24 is between abutment surfaces 42, 44, it is slidably coupled to the holder. The spring 30 urges the syringe flange into engagement with the first abutment surface 42.

One or more openings, such as openings 46A, 46B, are formed in the holder body. These openings are in opposing relation, and about ninety degrees offset from the axis including the maximum dimension of the holder flange 38. The openings extend between the first abutment surface 42 and a point nearly halfway to the first open end of the holder. The sizes of the openings are selected based upon the amount of flexibility desired in the holder body. Flexibility of the holder body or shield may also be provided by virtue of the materials which comprise these elements and the wall thicknesses thereof Each includes a relatively wide portion between the first abutment surface 42 and the flange 38.

A generally annular stop member 48 is provided on the holder in the form of an inwardly extending protrusion. Alternatively, a series of discrete protrusions (not shown) may be employed. The stop member is interrupted by the openings 46A, 46B, and includes an inclined surface facing the second open end of the holder body.

Figure 12B:
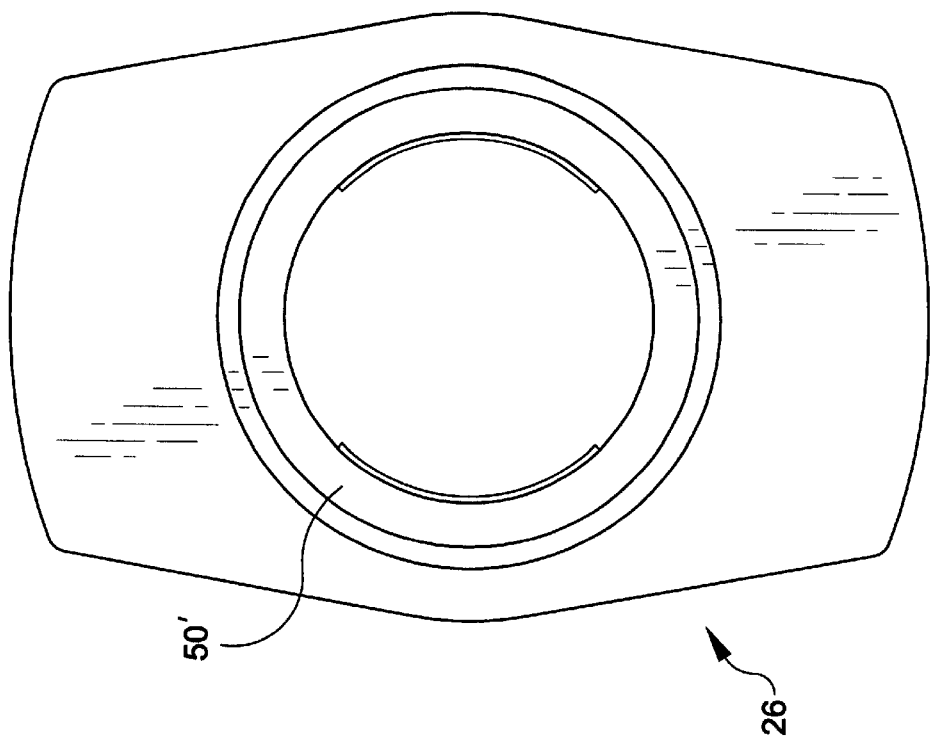
FIG. 12b is an end view of an alternative embodiment of the syringe holder.
Figure 12A:
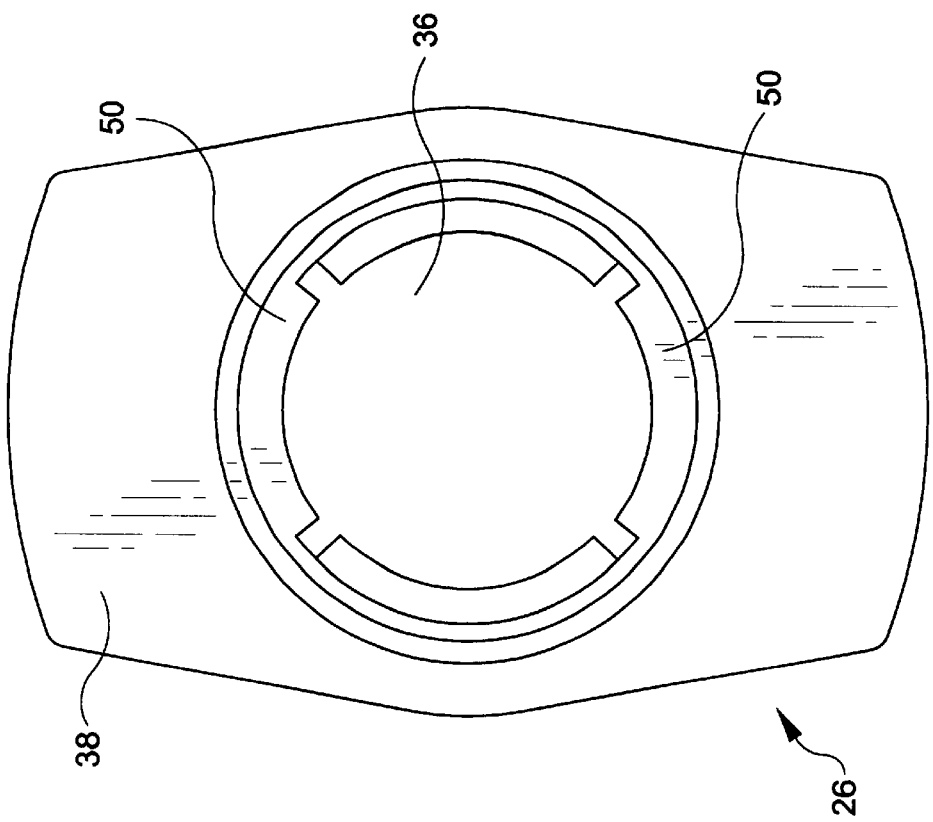
FIG. 12a is an end view of the syringe holder of the device.

A pair of first detents 50 are provided at or near the first open end of the holder. Each first detent is in the form of a projection extending radially inwardly from the body of the holder. As shown, in FIG. 12a, the first detents 50 are in opposing relation. Alternatively, a single, continuous detent in the form of an annular collar 50' may be provided, as shown in FIG. 12b.

A second pair of detents 52 are provided on the holder, and are axially spaced from the first detents. Each of these detents 52 is formed on an axially extending arm 54 which is integral with the holder body 34 and pivotable with respect thereto. The end surface of each detent facing the first open end of the holder is substantially perpendicular to the longitudinal axis of the holder. An inclined end surface is provided on the opposite side of each detent, and faces the second open end.

The shield 28 is comprised of a substantially cylindrical body 56. It is preferably small enough in diameter to be positioned within the holder, and large enough to fit over the barrel 16 of the syringe. A stop member 58 in the form of a radially outwardly extending collar is formed on the body 56 of the shield. This stop member has an inclined surface which is engageable with the inclined surface of the stop member 48 on the holder. Axially extending ribs 62 may be provided on the interior surface of the body for engaging a syringe barrel. Openings 60 in the shield provide flexibility for the shield body. The resilient engagement of the syringe barrel by the ribs allows the shield to slide with respect to the barrel without excess lateral play between the barrel and shield.

The spring 30 is sized to fit over the shield such that one end thereof bears against the shield stop member 58. The opposite end of the spring bears against the end fitting 32.

The spring may be used to cause the shield to move axially upon axial movement of the syringe barrel if it is fully compressed when the shield is in the retracted position. Direct engagement of the syringe flange 24 and shield, as provided in the preferred embodiment, would be unnecessary in such an arrangement. The operation of the device can be effected whether the shield, spring, end fitting and syringe barrel directly or indirectly engaged, so long as axial movement of the syringe barrel causes axial movement of the shield. As discussed below, the use of an end fitting is optional The end fitting 32 includes a cylindrical body 64 which can be inserted within the body 34 of the holder. One end of the spring 30 is insertable within the end fitting. An annular wall 66 is provided at one end of the cylindrical body 64, and is perferably integral therewith. This wall extends radially outwardly and radially inwardly with respect to the cylindrical body 64. The radially outwardly extending portion of the wall is adapted to engage the first abutment surface 42, so that it can be snapped behind the frustoconical portion at the second open end of the holder. It is used to maintain the spring 30 in position within the holder, thereby allowing the shield system to be manufactured as an assembly which does not include the syringe. The radially inwardly extending portion of the wall is adapted to engage between the first end of the spring 30 and the syringe flange 24. It will accordingly protect this flange from direct contact with the spring. Such protection is desirable where the shield system is used in conjunction with a glass syringe in order to prevent breakage. In the absence of the optional end fitting 32, the first abutment surface 42 will function to retain the syringe within the holder by engaging the syringe flange directly. The particular structure of the retaining member or members is unimportant so long as the syringe remains slidably coupled to the holder during use of the device. Axial movement of the syringe causes corresponding axial movement of the end fitting until the inwardly extending portion of the annular wall 66 engages the first end of the shield 28. In the absence of the end fitting, the syringe flange 24 would engage this surface directly.

Figure 13:
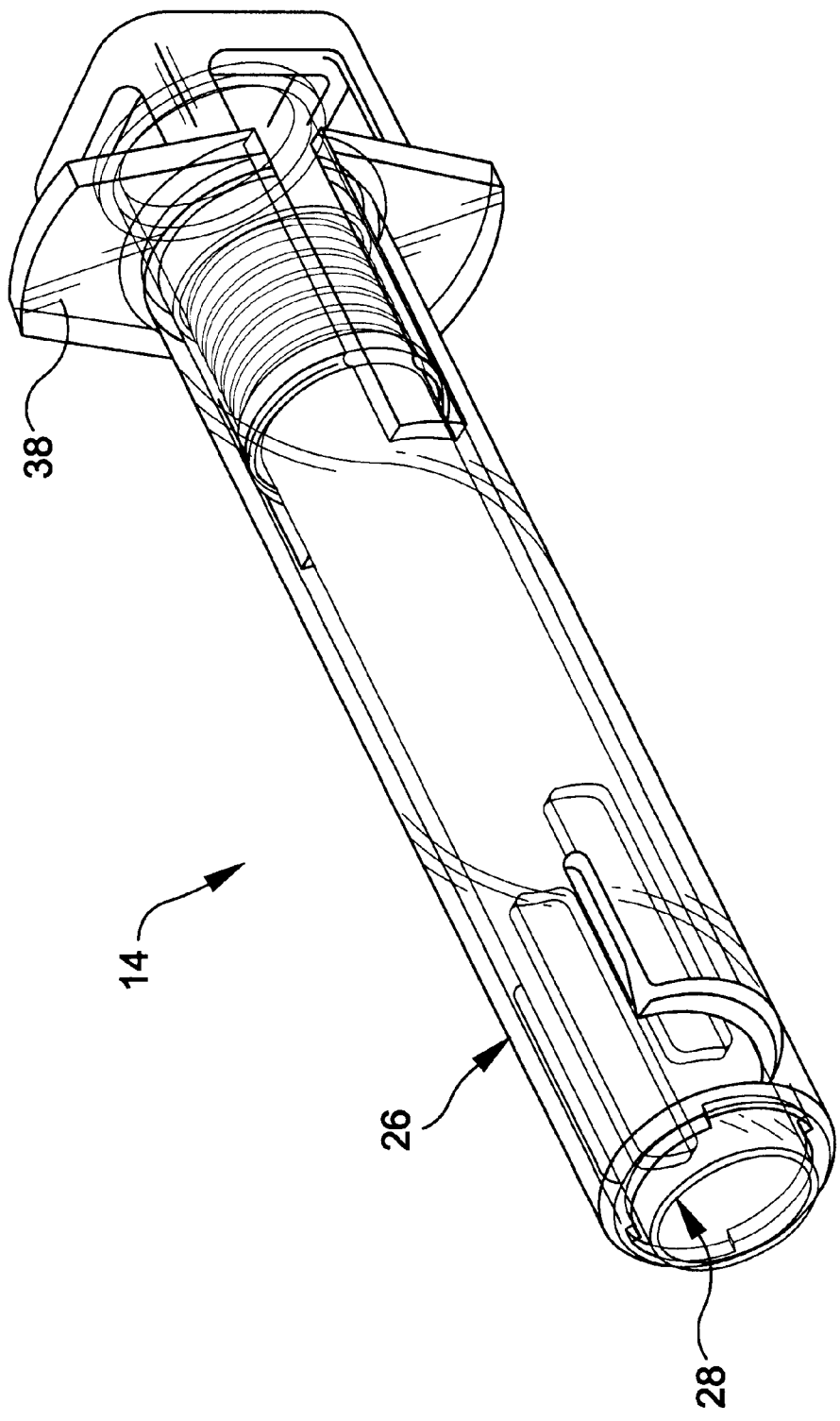
FIG. 13 is a perspective view of the shield system employed in the medical device shown in FIGS. 1–12.

The assembly and use of this preferred embodiment of the invention shall now be described. The shield 28 is slidably mounted to the holder by inserting it through the second open end thereof. The engagement of the stop members 48, 58 limits such insertion. The spring is inserted through the second open end of the holder, and over the shield until it abuts the shield stop member 58. As a final step prior to providing the shield system to the end user, the end fitting 32 is slipped over the exposed end of the spring and pushed through the second open end of the holder. The spring is substantially compressed during this step. The shield is resiliently urged towards the first open end of the holder while the end fitting is urged towards the second open end thereof Neither element can move due to the engagement of the stop members 48, 58, and the annular wall 66 with the first abutment surface 42, respectively. The force of the spring 30 is insufficient to cause the disengagement of these members. The shield system may be provided to end users or pharmaceutical manufacturers in the form shown in FIG. 13.

The shield system 14 receives a syringe of appropriate size through the second open end of the holder. The system as shown is designed for receiving a syringe including a flange. The syringe is inserted into the shield until the flange 24 snaps behind the first abutment surface 42. The end fitting 32 is displaced slightly during this procedure. As the needle of the syringe is ordinarily protected by a cover at this time, it may be safely coupled to the shield system.

The force required to disengage the stop members 48,58 should be greater than the force required to expel the contents of the syringe barrel. The plunger rod is employed to move the piston 20 down the syringe barrel until the contents of the barrel have been completely expelled. (The cover is, of course, removed prior to injection.) The contents of the barrel of a prefillable syringe ordinarily correspond to a single dose of the prescribed medicament.

Following removal of the needle 18 from the patient, the user applies a greater force to the plunger rod than that applied during injection. Such force causes axial displacement of the end fitting, the spring and the shield with respect to the holder. The distance between the annular wall 66 of the end fitting (or the flange 24) and the second abutment surface 44 is sufficient to allow the shield stop member 58 to move far enough axially to where its retention by the holder stop member 48 is overcome by the force of the spring. In the preferred embodiment, this is accomplished as the inclined surfaces of the stop members slide past each other. The holder stop member 48 is also displaced radially as such sliding occurs due to the flexibility of the holder body portion which adjoins it.

Figure 4:
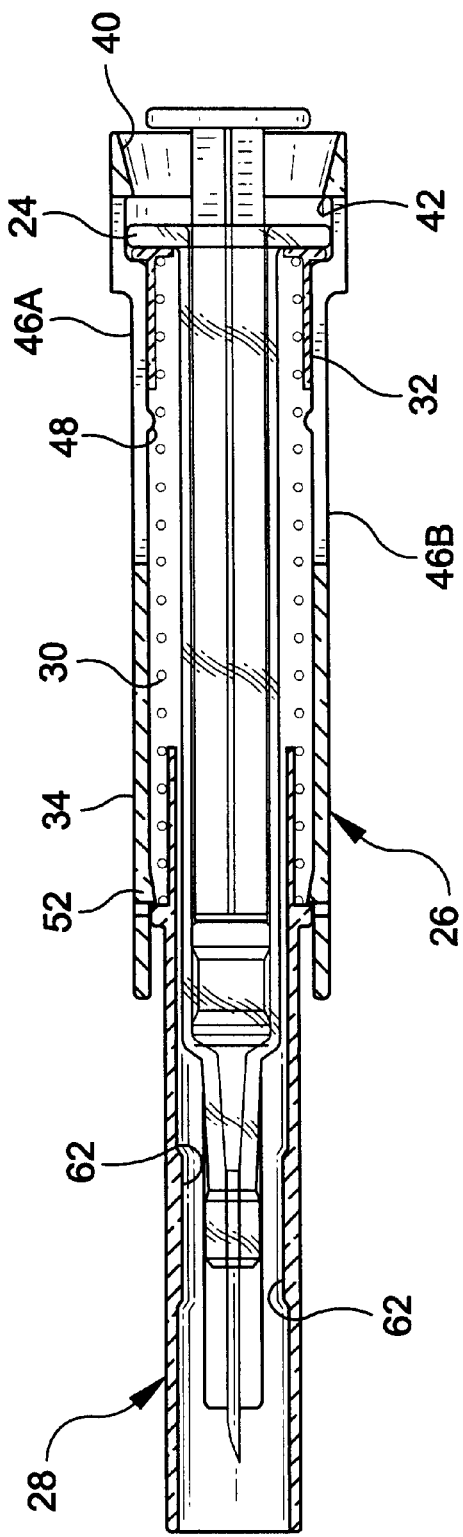
FIG. 4 is a sectional view thereof following actuation of the shield system of the device.
Figure 5:
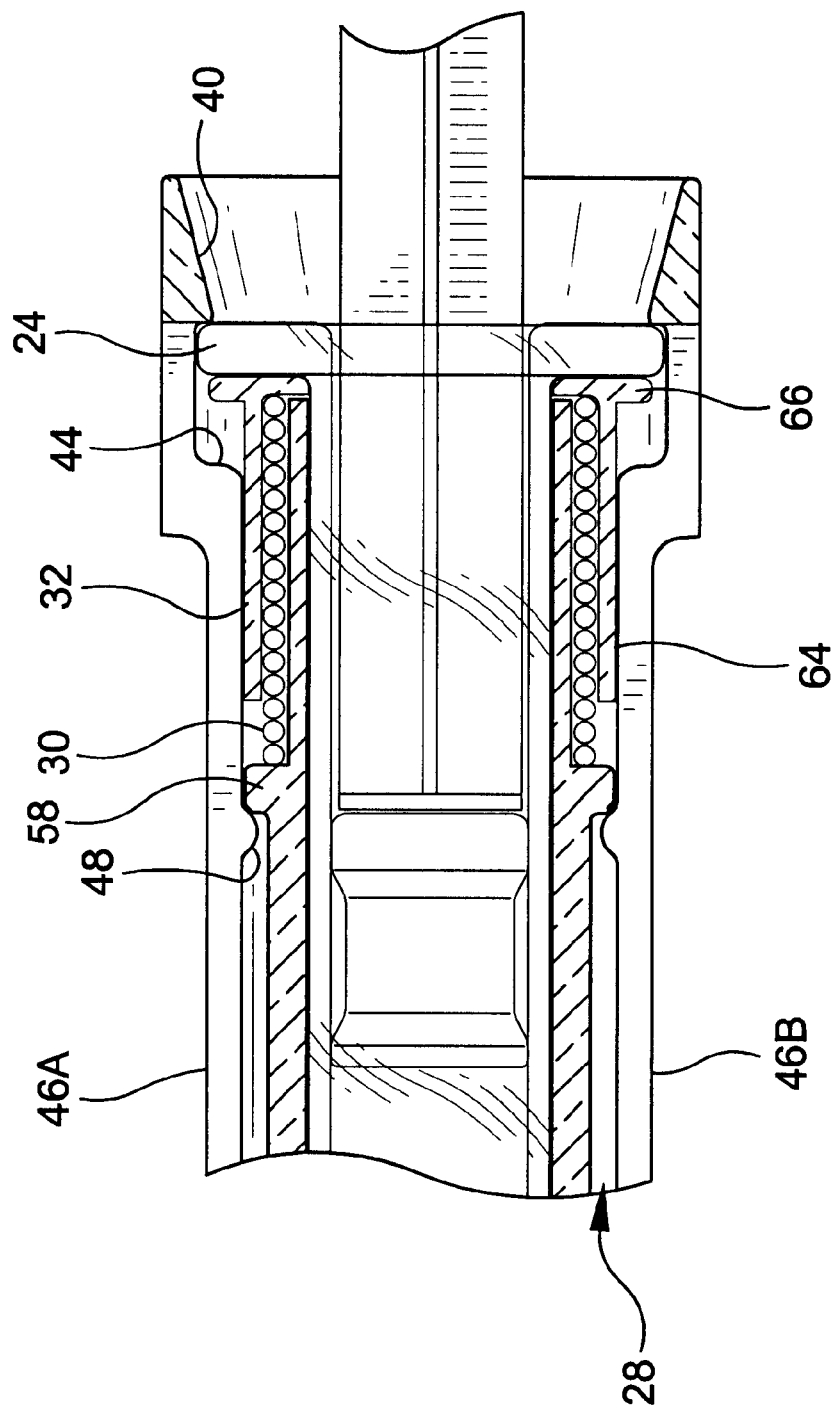
FIG. 5 is an enlarged sectional view of the proximal portion of the device prior to actuation of the shield system.
Figure 6:
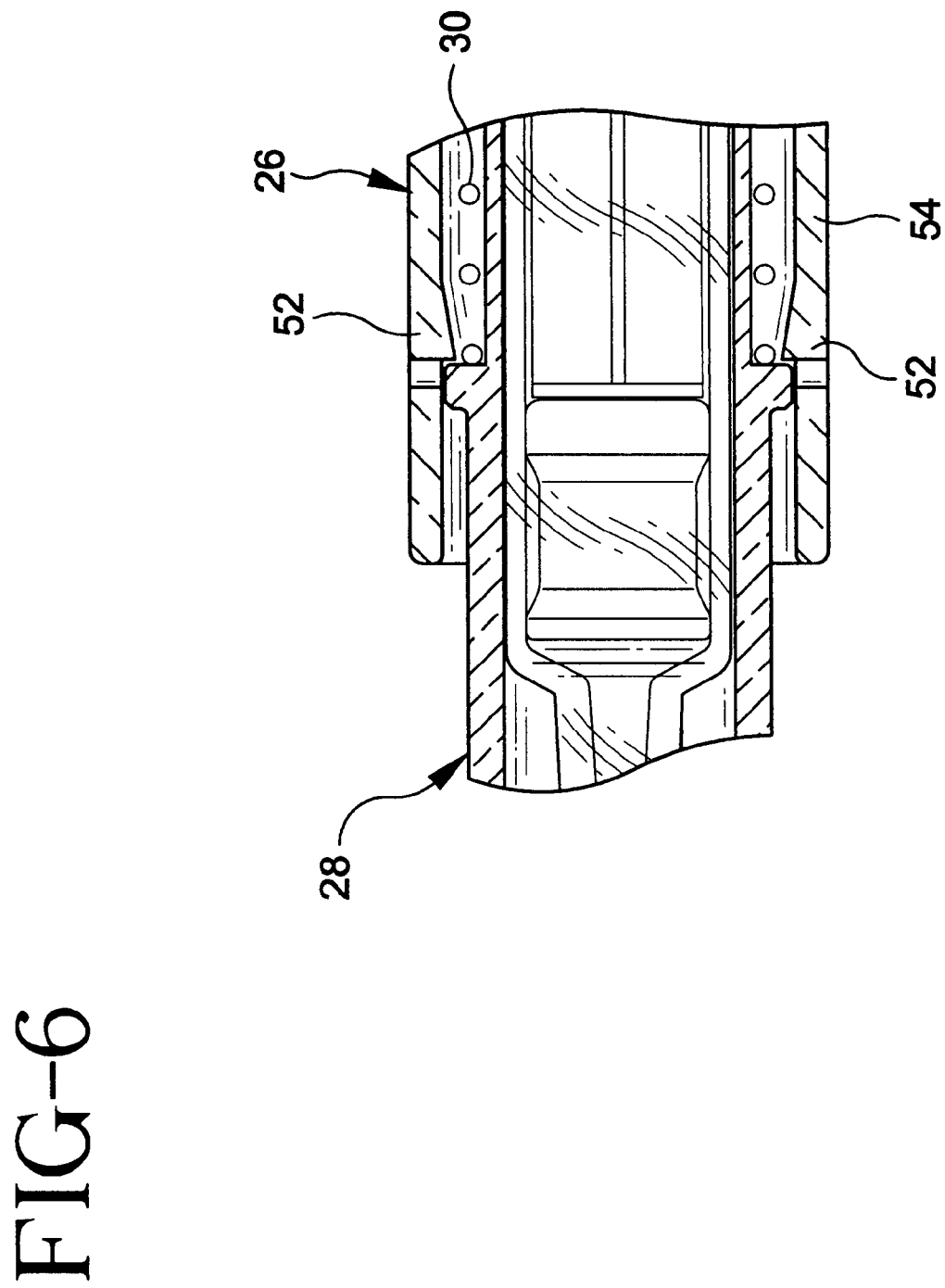
FIG. 6 is an enlarged sectional view showing a portion of the device, including the distal portion of a syringe holder of the device, following actuation of the shield system.
Figure 7:
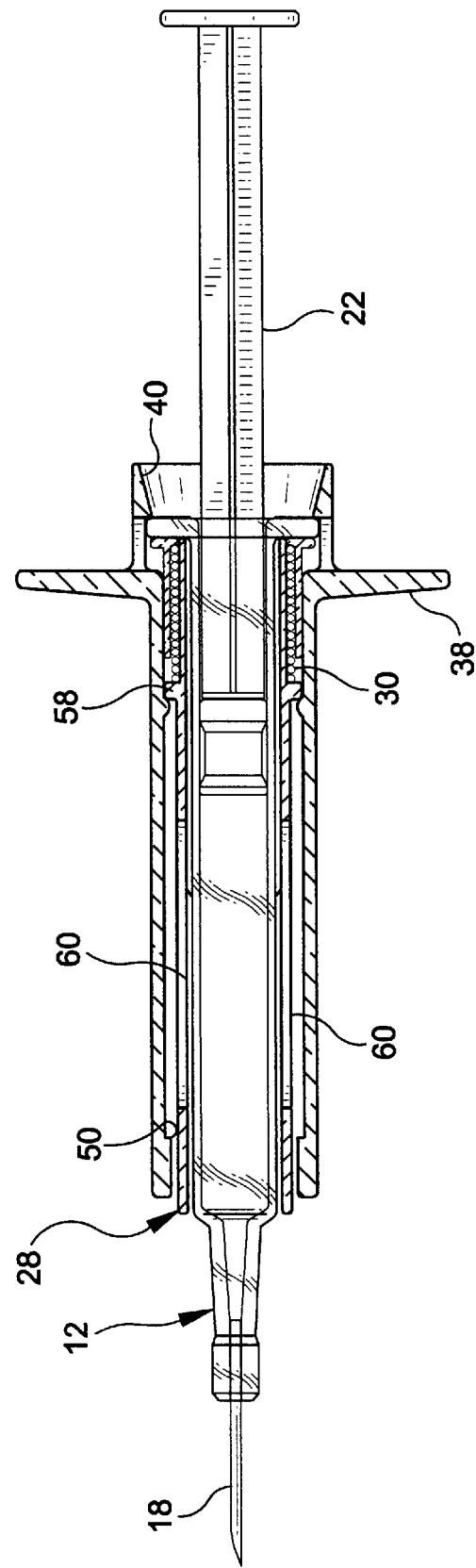
FIG. 7 is a sectional elevation view of the device rotated ninety degrees from the view provided in FIG. 3.
Figure 8:
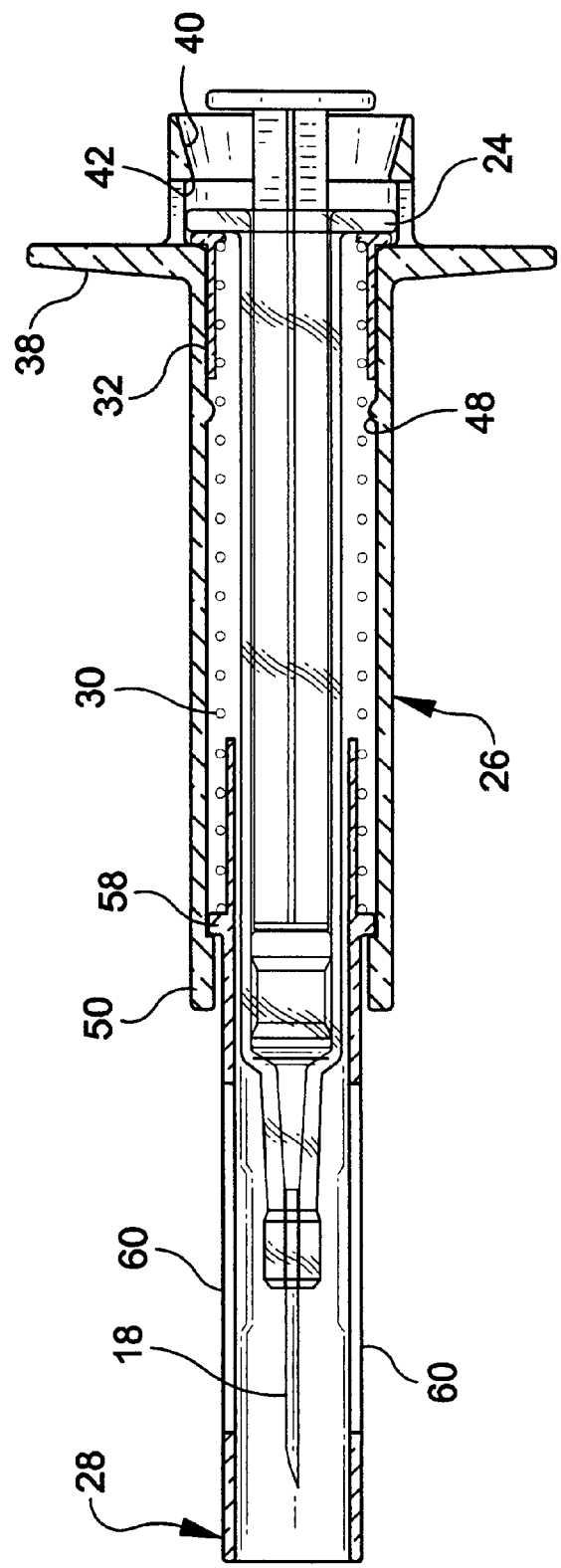
FIG. 8 is a sectional elevation view of the device following actuation of the shield system rotated ninety degrees from the view provided in FIG. 4.
Figure 9:
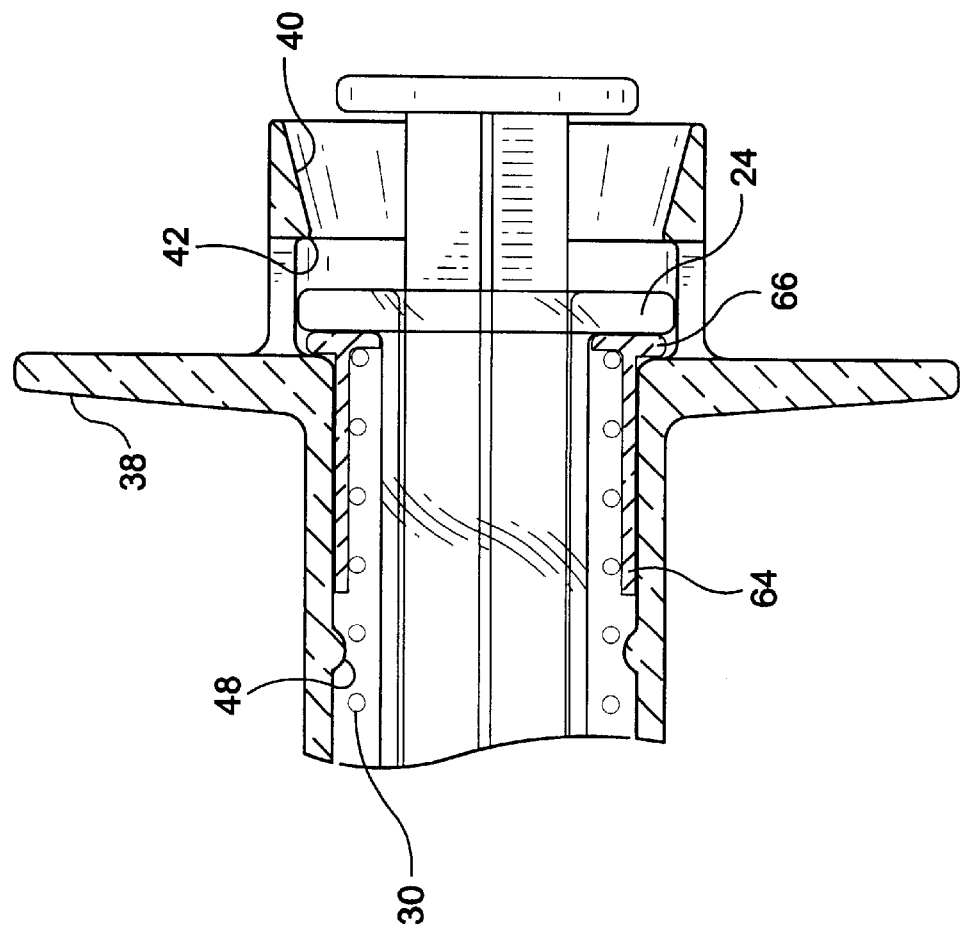
FIG. 9 is an enlarged sectional view of the proximal end portion of the device following actuation of the shield system.
Figure 10:
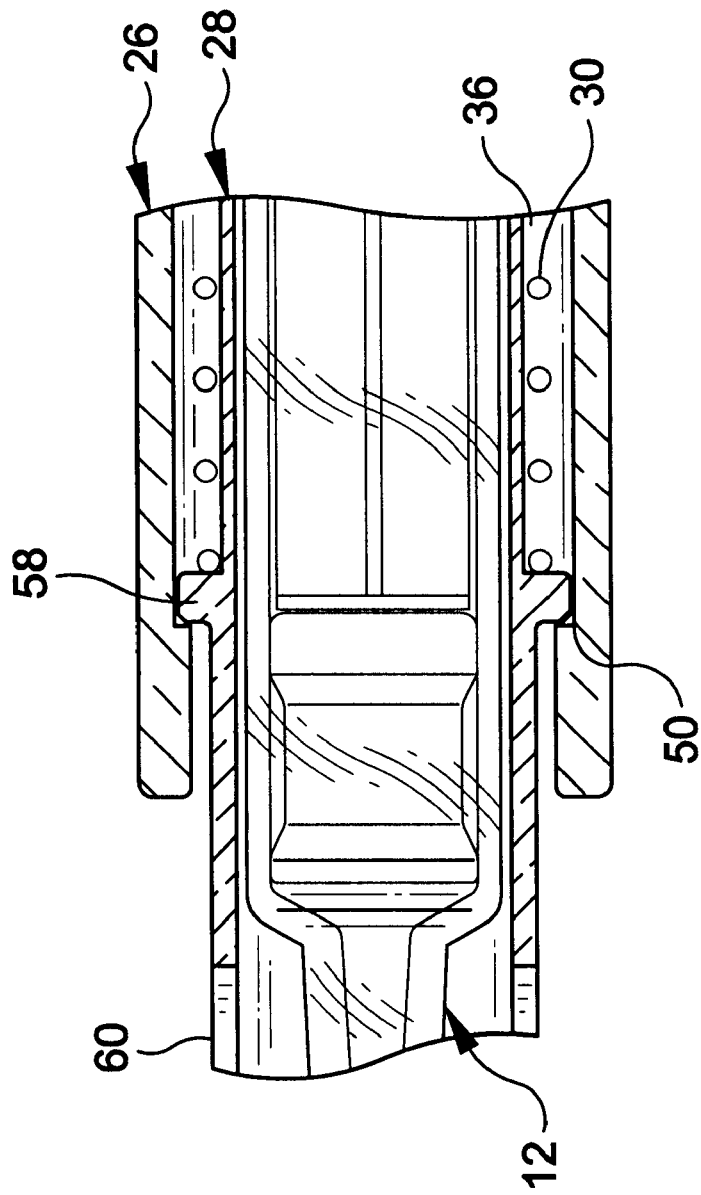
FIG. 10 is an enlarged sectional view similar to that shown in FIG. 6, but rotated ninety degrees with respect thereto.
Figure 11:
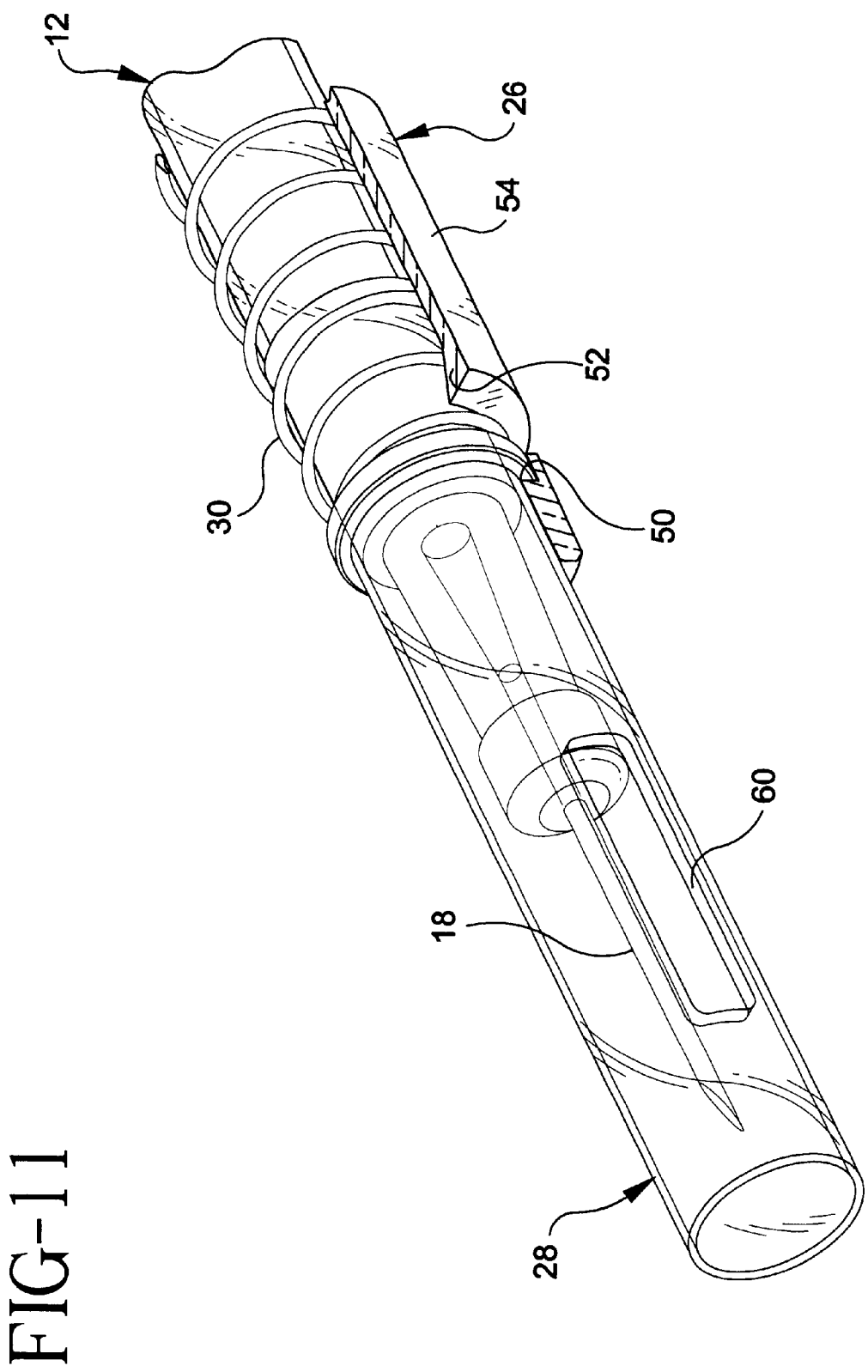
FIG. 11 is enlarged, partially cut-away perspective view showing the distal end of the device following actuation of the shield system.

Once the stop members 48, 58 are disengaged, the spring 30 expands rapidly, causing the shield to slide axially with respect to the holder and syringe barrel. The stop member 58 moves past the second detents 52, causing them to deflect radially outwardly and then inwardly to their original positions. It finally engages the first detents 50. Upon such engagement, the needle 18 is entirely and permanently covered by the shield, as shown in FIGS. 4 and 8. The shield cannot be retracted sufficiently to expose the needle tip due to the engagement of the stop member 58 with the second detents. It cannot be removed from the holder as the stop member 58 cannot move past the first detents 50.

The above-described procedure is particularly safe as it can be accomplished using only one hand. No second hand is required to push a button or use any other actuating member to release the spring. The risk of accidental actuation of the shield through inadvertent contact with an actuating button is eliminated. Moreover, a one-handed system is simpler for most people to use. It is readily apparent that the shield system can be adapted for use with syringes of various shapes and sizes without major modification.

The deployment of a shield in response to the axial displacement of a syringe barrel with respect to a holder is a safe and effective way of protecting against needle sticks. The preferred embodiment of the invention, as described above, provides advantages for the user as well as the manufacturer. The components are relatively easy to manufacture and assemble. It will be appreciated, however, that modifications can be made without changing the basic mode of operation of the device.

A second embodiment of the invention is shown in FIGS. 14–19. It is less preferred than the embodiment shown in FIGS. 1–11, but is still effective in providing the shielding of a needle or other like sharp-pointed instrument in response to the axial movement of the instrument. No end fitting is employed in this embodiment of the invention. The spring is instead held in position directly by the flange 24 of the syringe.

Figure 14:
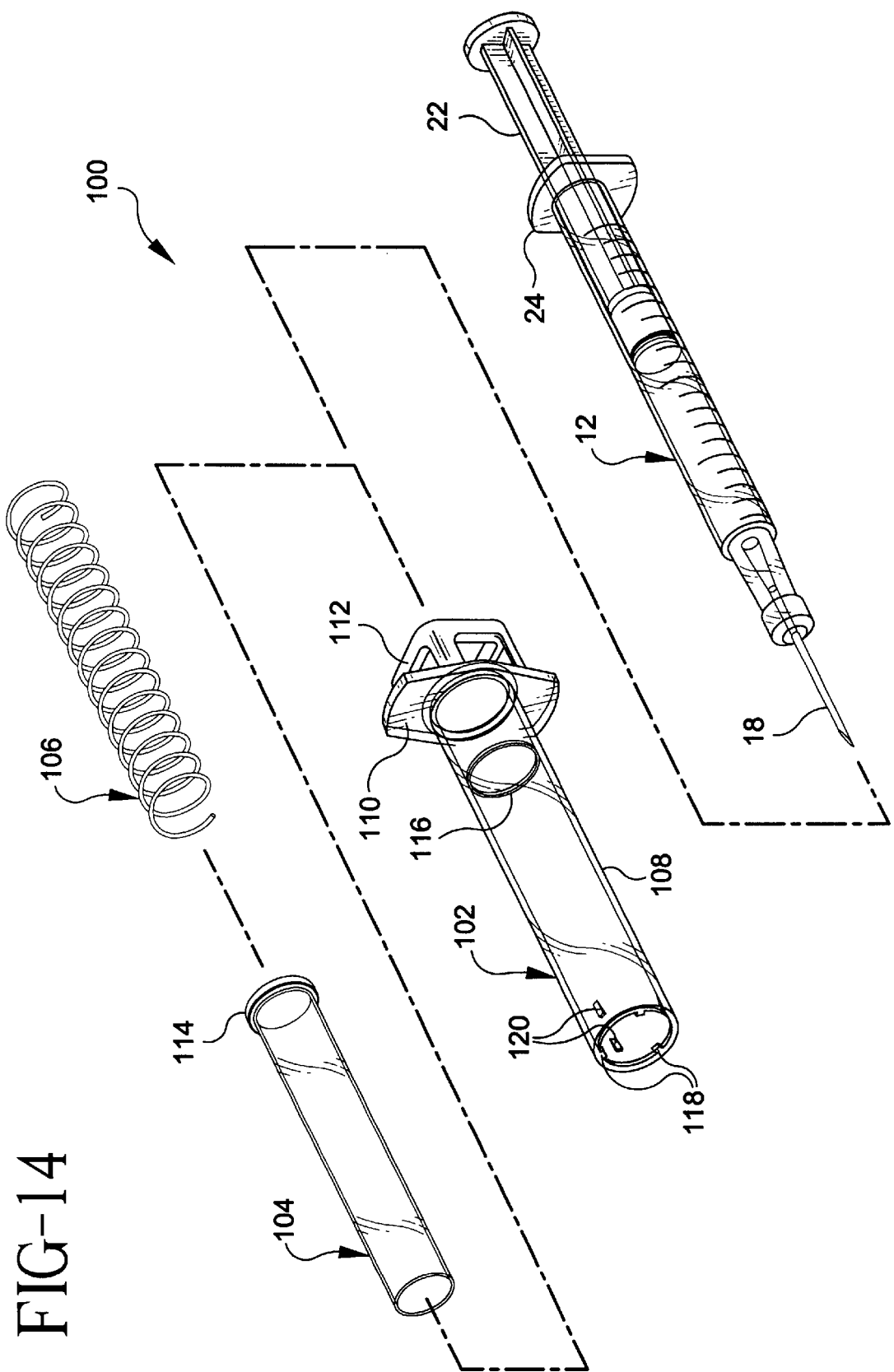
FIG. 14 is an exploded, perspective view showing a medical device according to a second embodiment of the invention.
Figure 15:
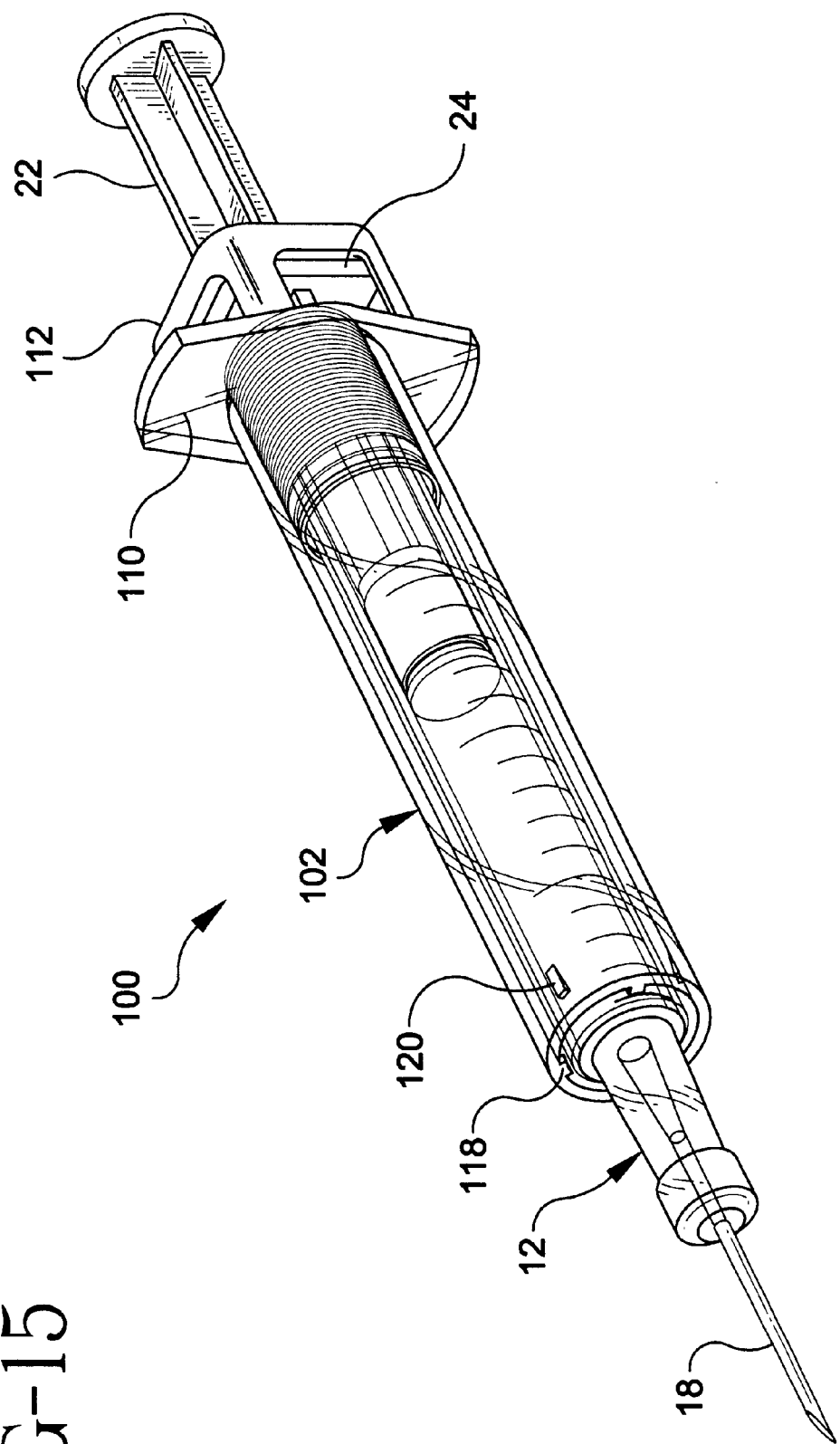
FIG. 15 is a perspective view thereof.

As shown in FIG. 14, a device 100 is provided which includes a syringe 12, a holder 102, a shield 104 and a coil spring 106. The holder 102 includes a cylindrical body 108 which defines a cylindrical enclosure for receiving the shield 104. The particular configuration of the holder is not critical so long as it is easily handled by the user of the device and accommodates the shield. A radially extending flange 110 is provided near one end of the holder. This end of the holder further includes a housing 112 for slidably retaining the flange 24 of the syringe similar to that used in the first embodiment 10 of the invention. The housing 112 includes two opposing surfaces which limit the distance the syringe flange may be moved with respect to the holder. The configuration of the housing may be modified to accommodate syringe flanges of various sizes and shapes.

Figure 16:
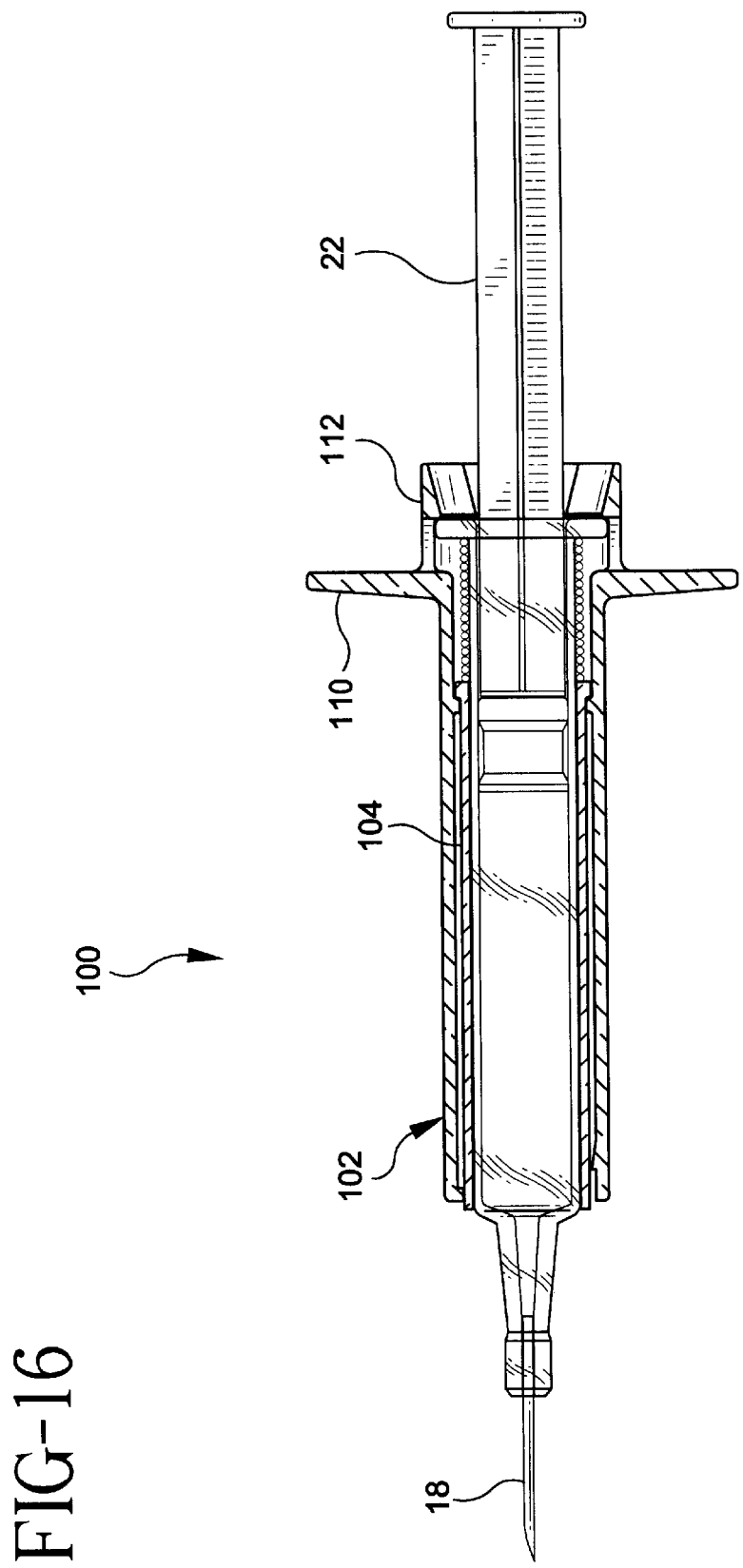
FIG. 16 is a sectional view thereof showing the device prior to actuation of the shield system thereof.

The spring 106 bears against the proximal end of the shield 104 and the distally facing surface of the syringe flange 24. The proximal end of the shield is radially enlarged, forming a collar 114. An annular stop member 116 is formed on the inner surface of the holder, and engages the collar 114 prior to use of the syringe. FIG. 16 shows the engagement of these structures. The coils of the spring are in substantially abutting relation when the syringe is in the position shown in this Figure.

The distal end of the holder includes at least a first set of detents 118 for preventing the shield 104 from being uncoupled from the holder once the collar 114 has been moved past the stop member 116. These detents are comprised of radially inwardly extending projections which are engageable with the collar 114. While the spring maintains the shield in the protective position over the needle 18, it is preferable to permanently maintain the shield in this position. A set of wedge-shaped detents 120 is accordingly provided on the inner surface of the holder. The second set of detents does not impede the passage of the collar 114 as the spring expands, but prevents retraction of the shield as the collar abuts the shoulder portions of the detents. One or both of the holder and shield preferably includes a degree of resiliency to facilitate operation of the detents as well as the collar and stop member.

Figure 17:
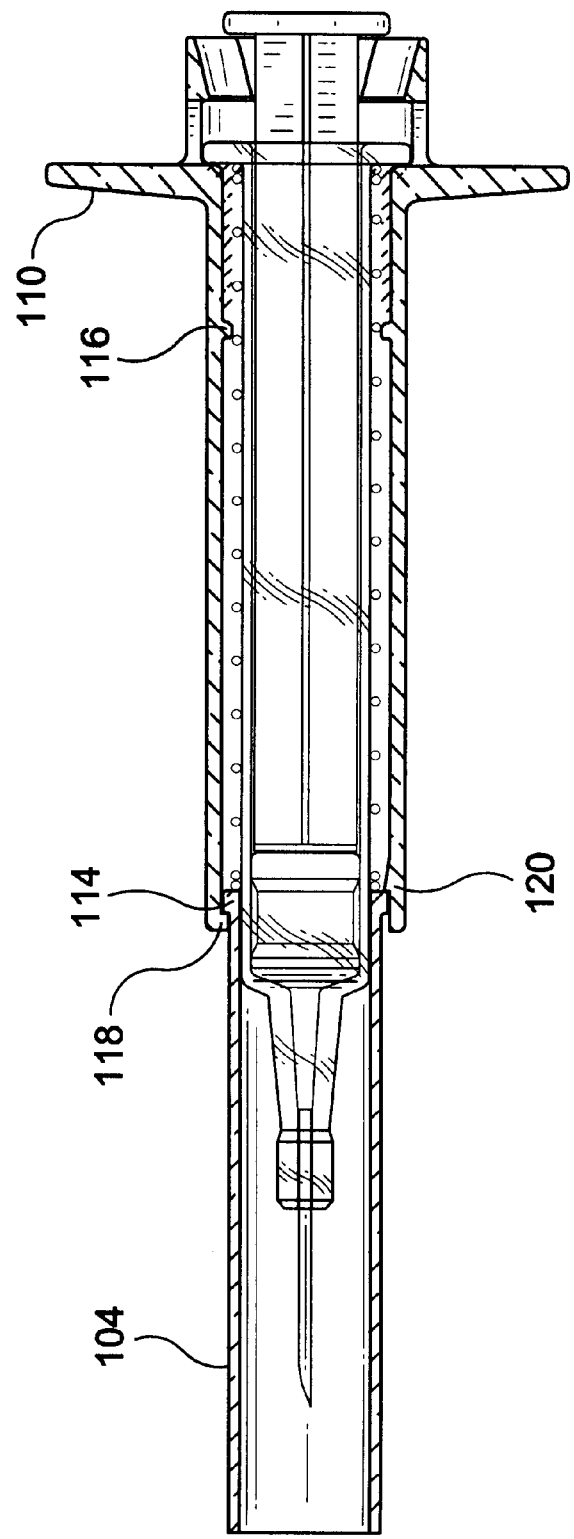
FIG. 17 is a sectional view showing the device following actuation of the shield system.
Figure 18:
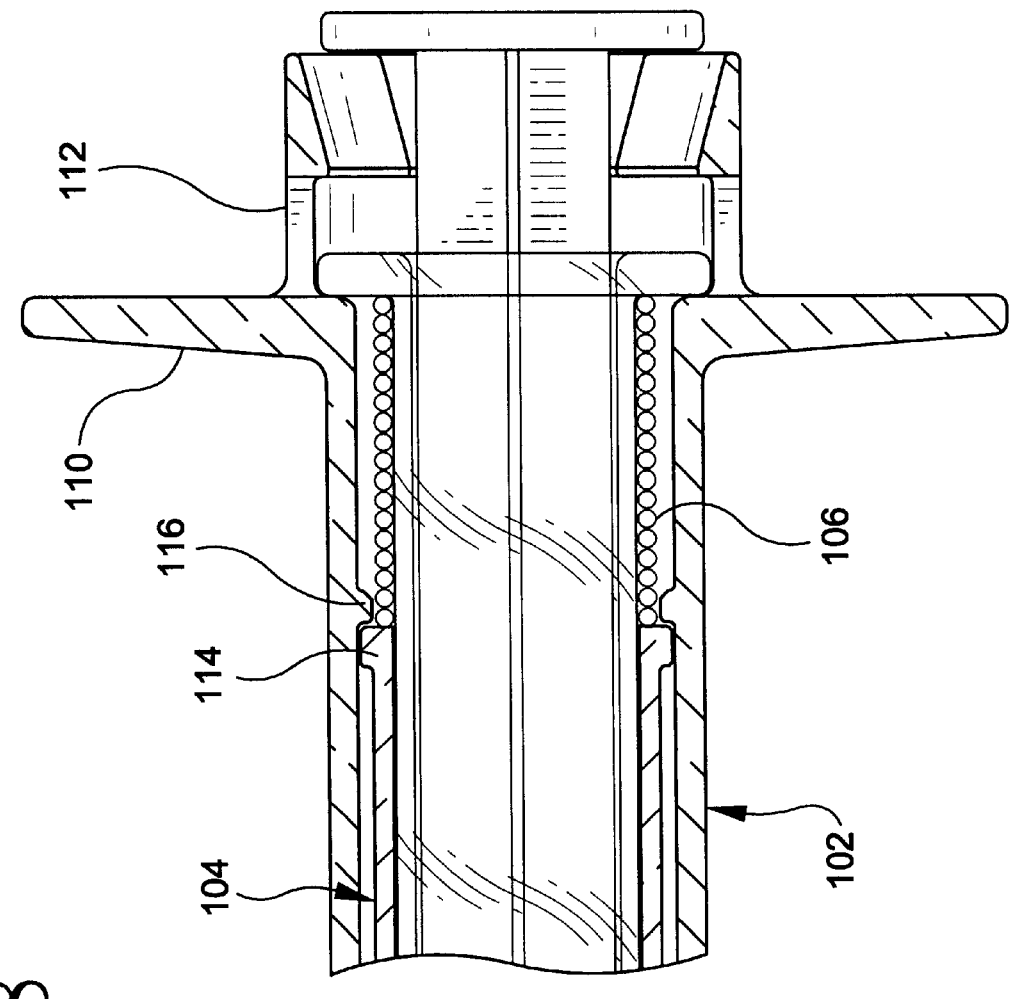
FIG. 18 is an enlarged sectional view of the proximal portion thereof immediately following actuation of the shield system.
Figure 19:
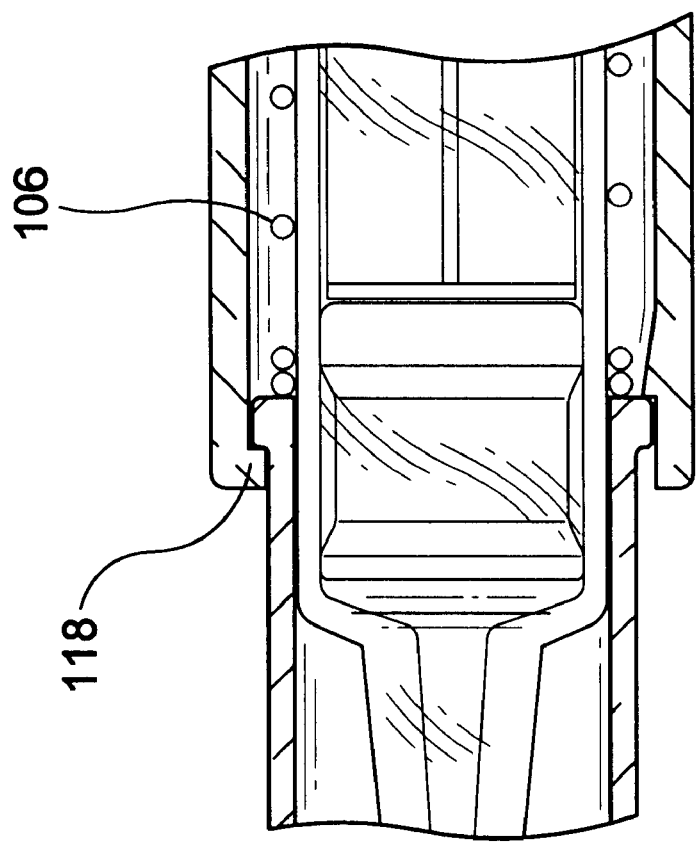
FIG. 19 is an enlarged sectional view showing a portion of the device following actuation of the shield system.

In operation, the device 100 is employed in substantially the same manner as a conventional syringe, starting with the arrangement of elements shown in FIG. 16. The user pushes the plunger rod using his thumb while the flanges of the holder are engaged by the index and middle fingers of the same hand. Once the piston has been moved to an abutting position with the end of the syringe barrel, further pressure exerted by the user on the plunger rod causes axial movement of the syringe itself. Due to the abutting relation of the coils of the spring to each other, the spring in effect forms a solid connection between the syringe flange and the proximal end of the shield. Axial movement of the syringe accordingly causes corresponding axial movement of the shield until the collar 114 moves beyond the stop member 116, as shown in FIG. 18. Expansion of the spring causes the shield to move to an extended position, as shown in FIG. 17.

It will be appreciated and understood by those skilled in the art that further and additional revisions to the invention may be devised without departing from the spirit and scope of the appended claims, the invention not being limited to the specific embodiments shown.

What is claimed is:

1. A medical device, comprising:
 a substantially cylindrical barrel;
 a needle connected to an end of said barrel;
 a holder comprising an elongate, generally cylindrical body including a first detent and a second detent, with said second detent being axially spaced from said first detent, said holder defining an enclosure with said barrel extending at least partially within said enclosure and being axially movable with respect to said holder;
 a retaining member positioned on said holder and engageable with said barrel with said barrel being slidably coupled to the holder during use of the device;
 a shield positioned about at least a portion of said barrel and positioned at least partially within said holder and connected to said holder, said shield being axially movable with respect to said holder between retracted and extended positions, and said shield including a third detent positionable between said first and second detents when said shield is in the extended position;
 a spring urging said shield towards its extended position;
 a first stop member positioned on said shield;
 a second stop member positioned on said holder and engageable with said first stop member when said shield is in its retracted position, the force of said spring being insufficient to cause disengagement of said first and second stop members; and
 said barrel being operationally coupled to said shield such that sufficient axial movement of said barrel in the direction of said needle causes axial movement of said shield sufficient to cause disengagement of said first and second stop members, allowing said spring to move said shield to the extended position.

2. A device as described in claim 1 wherein said shield is positioned within said holder, said first stop member extends radially outwardly from said shield, and said spring engages said first stop member.

3. A device as described in claim 2 wherein said second stop member extends radially inwardly from said holder.

4. A device as described in claim 3 wherein said holder includes a flexible wall portion adjoining said second stop member.

5. A device as described in claim 4 including an opening extending through said holder, said opening being axially proximal to said second stop member.

6. A device as described in claim 1 wherein said retaining member being slidably mounted to said holder and engaging an end of said barrel.

7. A device as described in claim 6 wherein said barrel includes a radially outwardly extending flange which engages said retaining member.

8. A device as described in claim 1 wherein said second detent is radially deflectable with respect to said holder.

9. A device as described in claim 1 wherein said third detent is comprised of said first stop member.

10. A device as described in claim 1 wherein said barrel includes a first radially outwardly extending flange, and said holder comprises an elongate, generally cylindrical body having first and second end portions, said second end portion including a second radially outwardly extending flange and means for slidably retaining said flange of said barrel.

11. A medical device, comprising:
- a generally cylindrical holder comprising an elongate body, an elongate enclosure defined by said body, first and second open ends, and first and second axially spaced and opposing abutment surfaces adjacent to said second open end;
- a syringe including a barrel, a needle secured to said barrel, a piston slidably positioned within said barrel, a plunger rod engaging said piston, and a radially outwardly extending flange positioned between said first and second abutment surfaces of said holder, said syringe being coupled to said holder and slidably positioned within said enclosure, said syringe being axially slidable within said enclosure;
- a generally cylindrical shield at least partially positioned within said enclosure and coupled to said holder, said shield being axially movable between a retracted position wherein said needle is at least partially exposed and an extended position wherein said shield covers said needle;
- a spring urging said shield towards the extended position;
- a stop member mounted to said holder and positioned to maintain said shield in the retracted position when said syringe is in a first axial position, wherein said spring urges said shield to the extended position when said syringe is moved to a sufficient distance towards said first open end of said holder.

12. A device as described in claim 11 wherein said shield includes a radially outwardly extending stop member, and said stop member of said holder extends radially inwardly, said holder further including first and second, radially inwardly extending detents, said first and second detents being positioned near said first open end of said holder and being axially spaced from each other, said radially inwardly extending stop member being positioned between said second open end of said holder and said second detent, said radially outwardly extending stop member of said shield being incapable of moving past said radially inwardly extending stop member of said holder under the force of said spring, but movable past said radially inwardly extending stop member of said holder under a force exceeding the force of said spring, said radially outwardly extending stop member of said shield being capable of moving past said second detent under the force of said spring and incapable of moving past said first detent, said second detent including a surface engageable with said radially outwardly extending stop member of said shield for preventing said shield from moving towards said first open end of said holder.

13. A device as described in claim 11 wherein said shield includes a radially outwardly extending stop member, and said stop member of said holder extends radially inwardly, said holder further including first and second, radially inwardly extending detents, said first and second detents being positioned near said first open end of said holder and being axially spaced from each other, said radially outwardly extending stop member of said shield being incapable of moving past said radially inwardly extending stop member of said holder under the force of said spring, but movable past said radially inwardly extending stop member of said holder under a force exceeding the force of said spring, said radially outwardly extending stop member of said shield being capable of moving past said second detent under the force of said spring and incapable of moving past said first detent, said second detent including a surface engageable with said radially outwardly extending stop member of said shield for preventing said shield from moving towards said first open end of said holder.

14. A device as described in claim 13 wherein said spring engages said radially outwardly extending stop member of said shield.

15. A device as described in claim 14 wherein said holder includes a flexible portion adjoining said radially inwardly extending stop member of said holder.

16. A device as described in claim 15 including an opening extending through said holder, said opening being axially proximal to said radially inwardly extending stop member of said holder.

17. A device as described in claim 13 further comprising a retaining member positioned on said holder and engageable with said syringe.

18. A device as described in claim 17 wherein said retaining member is slidably mounted to said holder and engaging an end of said syringe.

19. A device as described in claim 18 wherein said radially outwardly extending flange of said syringe engages said retaining member.

20. A device as described in claim 13 wherein said second detent is radially detectable with respect to said holder.

21. A device as described in claim 11 wherein said second open end of said holder includes a second radially outwardly extending flange.

* * * * *